(12) United States Patent
Ohshima et al.

(10) Patent No.: US 6,956,132 B2
(45) Date of Patent: Oct. 18, 2005

(54) PROCESS FOR PRODUCING 2-PHENYLACETOPHENONE DERIVATIVES AND PRECURSORS THEREFOR

(75) Inventors: Takeshi Ohshima, Shiga (JP); Shigeyuki Nishimura, Shiga (JP); Takayoshi Ando, Shiga (JP)

(73) Assignee: Ishihara Sangyo Kaisha. Ltd., Osaka (JP)

( * ) Notice: Subject to any disclaimer, the term of this patent is extended or adjusted under 35 U.S.C. 154(b) by 0 days.

(21) Appl. No.: 10/485,615

(22) PCT Filed: Jul. 15, 2002

(86) PCT No.: PCT/JP02/07176

§ 371 (c)(1),
(2), (4) Date: Jan. 30, 2004

(87) PCT Pub. No.: WO03/014051

PCT Pub. Date: Feb. 20, 2003

(65) Prior Publication Data

US 2004/0176644 A1 Sep. 9, 2004

(30) Foreign Application Priority Data

Aug. 3, 2001   (JP) .................................... 2001-236818

(51) Int. Cl.[7] .................. C07C 49/76; C07C 211/00
(52) U.S. Cl. ................. 568/335; 564/336; 564/373; 564/374
(58) Field of Search .............. 568/335; 564/336, 564/373, 374

(56) References Cited

U.S. PATENT DOCUMENTS

| | | | |
|---|---|---|---|
| 4,495,202 A | 1/1985 | Matsumoto et al. | 514/721 |
| 4,533,666 A | 8/1985 | Matsumoto et al. | 514/277 |
| 4,551,526 A | 11/1985 | Mai et al. | 544/163 |
| 5,011,998 A | 4/1991 | Hay | 564/384 |
| 5,017,723 A | 5/1991 | Aubard et al. | 564/383 |
| 5,543,573 A | 8/1996 | Takagi et al. | 514/590 |

FOREIGN PATENT DOCUMENTS

| | | | |
|---|---|---|---|
| JP | 52-90630 | | 7/1977 |
| JP | 01068758 | * | 3/1989 |
| JP | 64-68758 | | 3/1989 |
| JP | 2-13963 | | 1/1990 |
| JP | 4-270248 | | 9/1992 |
| JP | 5-279312 | | 10/1993 |
| JP | 2000-229903 | | 8/2000 |
| WO | 97/04778 | | 2/1997 |

OTHER PUBLICATIONS

Francesco Babudri, et al., "The reaction of arylaldehydes with hexamethylphosphorous triamide and the use of the resulting products for the synthesis of enamines and deoxybenzoins", Synthesis, No. 3, pp. 225–228 1991.

Martino Paventi, et al., "facile preparation of deoxybenzoins via a novel synthesis of enamines", Tetrahedron Letters, vol. 32, No. 13, pp. 1617–1620 1991.

Roberto Olivera, et al., "A convenient strategy for the synthesis of 4,5–bis (o–haloaryl)isoxazoles", Journal of Organic Chemistry, vol. 65, No. 20, pp. 6398–6411 2000.

* cited by examiner

Primary Examiner—Johann Richter
Assistant Examiner—Sikarl A. Witherspoon
(74) Attorney, Agent, or Firm—Oblon, Spivak, McClelland, Maier & Neustadt, P.C.

(57) ABSTRACT

A process for producing 2-phenylacetophenone derivatives represented by the formula (I):

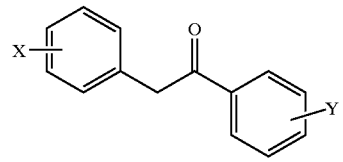

(wherein X is an alkyl group or a haloalkyl group, and Y is a hydrogen atom, a halogen atom or an alkyl group which may be substituted), which comprises reacting a compound represented by the formula (II):

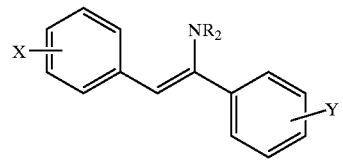

(wherein X and Y are as defined above, and R is a hydrogen atom or an alkyl group) with an acid.

20 Claims, No Drawings

PROCESS FOR PRODUCING 2-PHENYLACETOPHENONE DERIVATIVES AND PRECURSORS THEREFOR

TECHNICAL FIELD

The present invention relates to a process for producing 2-phenylacetophenone derivatives represented by the after-mentioned formula (I) which are useful as intermediates for various chemical products, pharmaceuticals and agricultural chemicals, and precursors for the production thereof.

BACKGROUND ART 2-phenylacetophenone derivatives represented by the after-mentioned formula (I) are disclosed, for example, in JP-A-5-279312, JP-A-4-270248 and Japanese Patent No. 2,805,255, and they can be produced by conventional methods and also by the methods disclosed in these publications. However, by these production methods, it has been difficult to produce the derivatives depending upon the types of the substituents X, Y and R or the positions to be substituted, or they can be produced only by a complicated production process involving many reaction steps. Further, a process proposed to solve such problems as disclosed in JP-A-2000-229903, employs an expensive transition metal catalyst, and in an industrial operation, the catalyst is required to be recovered and reused.

Compounds similar to the compounds represented by the after-mentioned (II) as the precursors for the production of 2-phenylacetophenone derivatives of the present invention are disclosed, for example, in J. Org. Chem. 2000, 65, 6398–6411, JP-A-60-13730, JP-A-60-13759, JP-A-2-13963 and JP-A-11-510163, but the compounds represented by the formula (II) are not disclosed.

DISCLOSURE OF THE INVENTION

It is an object of the present invention to produce 2-phenylacetophenone derivatives which used to be difficult to industrially produce by conventional methods, efficiently and in a short reaction process by using starting materials which are industrially readily and inexpensively available.

The present invention provides a process for producing 2-phenylacetophenone derivatives represented by the formula (I):

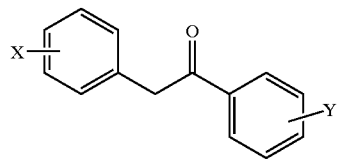

(wherein X is an alkyl group or a haloalkyl group, and Y is a hydrogen atom, a halogen atom or an alkyl group which may be substituted), characterized by reacting a compound represented by the formula (II):

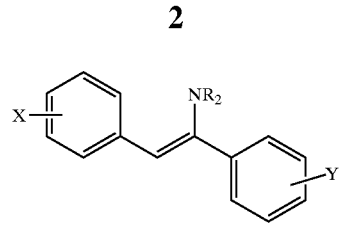

(wherein X and Y are as defined above, and R is a hydrogen atom or an alkyl group) with an acid.

Further, the present invention provides such a process for producing 2-phenylacetophenone derivatives, which comprises:

(1) a first stage of reacting a compound represented by the formula (III):

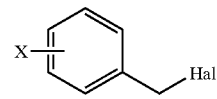

(wherein X is an alkyl group or a haloalkyl group, and Hal is a halogen atom) with a compound represented by the formula (IV):

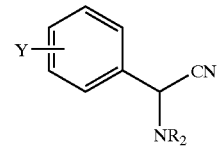

(wherein Y is a hydrogen atom, a halogen atom or an alkyl group which may be substituted; and R is a hydrogen atom or an alkyl group) in the presence of a base and a solvent, to produce a compound represented by the formula (II):

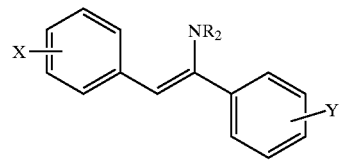

(wherein X, Y and R are as defined above); and (2) a second stage of reacting the compound of the formula (II) produced in the first stage with an acid to produce a 2-phenylacetophenone derivative represented by the formula (I):

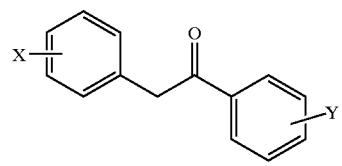

(wherein X and Y are as defined above).

Further, the present invention provides a compound represented by the formula (II):

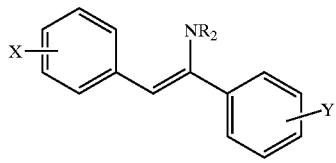

(wherein X is an alkyl group or a haloalkyl group, Y is a hydrogen atom, a halogen atom or an alkyl group which may be substituted, and R is a hydrogen atom or an alkyl group), as a precursor for the production of the above-mentioned 2-phenylacetophenone derivatives.

BEST MODE FOR CARRYING OUT THE INVENTION

In the present invention, the alkyl group or the alkyl moiety represented by X and Y contained in the formulae (I) and (II) may preferably be one having from 1 to 6 carbon atoms, such as methyl, ethyl, n-propyl, isopropyl, n-butyl, t-butyl, pentyl or hexyl. The halogen atom may be an atom of fluorine, chlorine, bromine or iodine.

The substituent for the alkyl group which may be substituted, represented by Y in the formulae (I) and (II), may preferably be a halogen atom; an alkoxy group which may be substituted by halogen atom(s); or an alkylthio group which may be substituted by halogen atom(s). The number of such substituents may be 1 or more, and in the case of more than 1, such substituents may be the same or different. Further, the alkyl moiety of the above alkoxy or alkylthio group may preferably be one having from 1 to 6 carbon atoms, and the halogen atom may be an atom of fluorine, chlorine, bromine or iodine.

X contained in the formulae (I) and (II) is preferably a haloalkyl group, or preferably an alkyl group substituted by fluorine atoms, particularly preferably difluoromethyl, trifluoromethyl, 2,2,2-trifluoromethyl or heptafluoropropyl, most preferably trifluoromethyl. Further, Y contained in the formulae (I) and (II) is preferably a halogen atom, most preferably a fluorine atom.

The alkyl group represented by R contained in the formula (II) is preferably one having from 1 to 6 carbon atoms, such as methyl, ethyl, n-propyl, isopropyl, n-butyl, t-butyl, pentyl or hexyl.

The compound of the formula (II) may be in the form of a salt with an acidic substance or a basic substance. The salt with an acidic substance may, for example, be an inorganic salt such as a hydrochloride or a sulfate, and, the salt with a basic substance may be a salt with an inorganic base or an organic base, such as a sodium salt, a potassium salt, a calcium salt, an ammonium salt or a dimethyl ammonium salt.

The process of the present invention comprises a first stage of reacting the compound of the formula (III) with the compound of the formula (IV) in the presence of a base and a solvent to produce the compound of the formula (II), and a second stage reaction of reacting the compound of the formula (II) with an acid to produce the compound of the formula (I). The reactions of the respective stages will be described in detail hereinafter. Here, the compound of the formula (II) as the reaction product in the first stage is a novel compound. Further, this compound has geometrical isomers i.e. E-isomer and Z-isomer, and such respective isomers and a mixture of the isomers are within the scope of the present invention.

In the reaction of the first stage, the amounts of compounds of the formulae (III) and (IV) to be used, vary depending upon the types of the respective compounds, the differences in the reaction conditions which will be described hereinafter, etc., and can not generally be defined. However, usually, the compound of the formula (IV) is used in a proportion of from 0.9 to 5.0 mols, preferably from 0.9 to 1.5 mols, more preferably from 0.9 to 1.0 mol, per mol of the compound of the formula (III). When the amounts of both compounds are equimolar amounts or in the vicinity thereof, the compound of the formula (II) can be obtained in good yield, such being industrially advantageous from the viewpoint of e.g. the production costs.

The reaction temperature and the reaction time in the reaction of the first stage, vary depending upon the types of the compounds of the formulae (III) and (IV) and the differences in the reaction conditions which will be described hereinafter, and can not generally be defined. However, usually, the reaction temperature is from 0 to 100° C., preferably from 0 to 40° C. Even when the reaction temperature is room temperature or in its vicinity, the compound of the formula (II) can be obtained in good yield, such being industrially advantageous from the viewpoint of e.g. the production costs. Further, the reaction time is usually from 0.1 to 24 hours, preferably from 1 to 6 hours.

The base which can be used for the reaction of the first stage may, for example, be a hydride of an alkali metal such as sodium hydride or potassium hydride; or an organic metal compound such as n-butyllithium. It is particularly preferred to use a hydride of an alkali metal, and it is especially preferred to use sodium hydride. The base is used usually in a proportion of from 1.0 to 2.0 mols, preferably from 1.0 to 1.5 mols, more preferably from 1.0 to 1.3 mols, per mol of the compound of the formula (III). Even if the amount of the base to be used is an equimolar amount with the compound of the formula (III) or in its vicinity, the compound of the formula (II) can be obtained in good yield, such being industrially advantageous from the viewpoint of e.g. the production costs.

The solvent which can specifically be used in the reaction of the first stage may, for example, be an ether such as tetrahydrofuran or dioxane; an aprotic polar solvent such as dimethylformamide, dimethylacetamide, N-methyl-2-pyrrolidone, dimethylsulfoxide or sulfolane; an aromatic hydrocarbon such as toluene or chlorobenzene; or an aliphatic hydrocarbon. It is especially preferred to use an aprotic polar solvent, and it is most preferred to use dimethylformamide.

The reaction of the first stage is preferably carried out in an inert gas atmosphere. As a specific inert gas to be used, any gas inert to the reaction such as nitrogen, argon or helium may be used.

At the time of setting each of the above-mentioned various conditions for the reaction of the first stage, i.e. the amounts of the compounds of the formulae (III) and (IV), various reaction conditions which vary depending upon the types of the compounds of the formulae (III) and (IV), the reaction temperature and the reaction time, numerical values are optionally selected within the usual ranges and the preferred ranges shown for the respective conditions and may be suitably combined.

The compound of the formula (IV) as the starting material of the reaction of the first stage is a compound disclosed in e.g. JP-A-52-90630, U.S. Pat. No. 4,551,526 or U.S. Pat. No. 5,017,723. However, a compound represented by the formula (IV'):

(wherein R is a hydrogen atom or an alkyl group) is not specifically disclosed in these prior art references.

The compound of the formula (IV) can be produced by a method in accordance with the disclosure in column 15, lines 20 to 62 of U.S. Pat. No. 5,017,723. Specifically, it can be produced by reacting a compound represented by the formula (V):

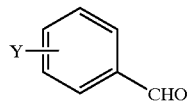

(wherein Y is a hydrogen atom, a halogen atom or an alkyl group which may be substituted) with a compound represented by the formula (VI): M-CN (wherein X is an alkali metal element) and a compound represented by the formula (VII): $R_2NH$ (wherein R is a hydrogen atom or an alkyl group) or its salt.

The compound represented by the formula (VI) is preferably sodium cyanide or potassium cyanide.

The reaction of the compound of the formula (V) with the compound of the formula (VI) and the compound of the formula (VII) is carried out in the presence of an acid. As such an acid, a mineral acid such as hydrochloric acid or sulfuric acid may be mentioned. In such a case, the acid is used usually in a proportion of from 0.2 to 1.0 mol per mol of the compound of the formula (VII).

Further, in a case where the compound of the formula (V) is reacted with the compound of the formula (VI) and a salt of the compound of the formula (VII), the salt of the compound of the formula (VII), may, for example, be a salt with a mineral acid such as hydrochloric acid or sulfuric acid.

In the above-mentioned method for producing the compound of the formula (IV), the amounts of the compounds of the formulae (V), (VI) and (VII) vary depending upon the types of the respective compounds, the differences in the reaction conditions which will be described hereinafter, etc. and can not generally be defined. However, the compound of the formula (VI) is used usually in a proportion of from 0.8 to 3.0 mols per mol of the compound of the formula (V). Further, the compound of the formula (VII) is used usually in a proportion of from 0.8 to 3.0 mols per mol of the compound of the formula (V).

The reaction temperature and the reaction time in the reaction for producing the compound of the formula (IV) vary depending upon the types of the compounds of the formulae (V), (VI) and (VII), the differences in the reaction conditions which will be described hereinafter, etc. and can not generally be defined. However, the reaction temperature is usually within a range of from 5° C. to the reflux temperature. Further, the reaction time is usually from 1 to 24 hours.

The above-described reaction for producing the compound of the formula (IV) is preferably carried out in the presence of a solvent. The solvent which can specifically be used, may, for example, be water; an alcohol such as methanol; a mixed solvent of water with an alcohol; aceto-nitrile; or an aromatic hydrocarbon such as toluene or chlorobenzene.

At the time of setting each of the above-mentioned various conditions in the reaction for producing the compound of the formula (IV) i.e. the amounts of the compounds of the formulae (V), (VI) and (VII), various reaction conditions which vary depending upon the types of the compounds of the formulae (V), (VI) and (VII), the reaction temperature and the reaction time, numerical values are optionally selected within the usual ranges and the preferred ranges shown for the respective conditions and may be suitably combined.

After completion of the reaction in the first stage, the compound of the formula (II) may be isolated from the reaction system by a usual method and may be purified by a distillation method, a recrystallization method or the like, as the case requires. The compound of the formula (II) thus isolated and purified, can be supplied as the starting material for the reaction of the second stage. However, the compound of the formula (II) can be subjected to the reaction of the second stage without isolating or purifying it from the reaction system for the reaction in the first stage, and accordingly, the reaction of the first stage and the reaction of the second stage can be carried out continuously in the same reactor, whereby the production cost can be reduced, such being industrially advantageous.

As the acid to be used for the reaction of the second stage, a mineral acid such as hydrochloric acid, sulfuric acid, nitric acid, hydrobromic acid or phosphoric acid; or an organic acid such as acetic acid or propionic acid, may, for example, be mentioned. It is particularly preferred to use a mineral acid, and among mineral acids, it is especially preferred to use hydrochloric acid or sulfuric acid. The amount of the acid to be used varies depending upon the type of the compound of the formula (II) and the differences in the reaction conditions which will be described hereinafter and can not generally be defined. However, it is used usually in a proportion of from 1 to 30 mols, preferably from 1.5 to 15 mols, more preferably from 1.5 to 8 mols, per mol of the compound of the formula (II).

The reaction temperature and the reaction time for the reaction of the second stage vary depending upon the type of the compound of the formula (II) and the differences in the reaction conditions which will be described hereinafter and can not generally be defined. However, the reaction temperature is usually from 25 to 140° C., preferably from 70 to 120° C. Further, the reaction time is usually from 0.1 to 24 hours, preferably from 0.3 to 4 hours.

The reaction of the second stage is preferably carried out in the presence of a solvent. The solvent which can specifically be used, may, for example, be water; an alcohol such as methanol; or a solvent which is used in the first stage. Further, in a case where an acid which functions also as a solvent, such as acetic acid, is used, it can be used as both an acid and a solvent.

At the time of setting each of the above-mentioned various conditions in the second stage, i.e. the amounts of the compound of the formula (II) and the acid, various reaction conditions which vary depending upon the type of the compound of the formula (II) and the acid, the reaction temperature and the reaction time, numerical values are optionally selected from the usual ranges and the preferred ranges shown for the respective conditions and may be suitably combined. Further, various conditions in the first stage and various conditions in the second stage may suitably be combined.

After completion of the reaction of the second stage, the 2-phenylacetophenone derivative of the formula (I) can be isolated from the reaction system by a usual method and, if necessary, can be purified by a distillation method, a recrystallization method or the like.

Now, some of preferred embodiments in the present invention will be exemplified.

(1) A process which comprises reacting a compound of the formula (II) with an acid to produce a 2-phenylacetophenone derivative of the formula (I).

(2) The process of (1) which comprises a first stage of reacting a compound of the formula (III) with a compound of the formula (IV) in the presence of a base and a solvent to produce a compound of the formula (II); and a second stage of reacting the compound of the formula (II) produced in the first stage, with an acid to produce a 2-phenylacetophenone derivative of the formula (I).

(3) The process of (2) which comprises a first stage of reacting a compound of the formula (V) with a compound of the formula (VI) and a compound of the formula (VII) or its salt, to produce a compound of the formula (IV), which is reacted with a compound of the formula (III) in the presence of a base and a solvent, to produce a compound of the formula (II); and a second stage of reacting the compound of the formula (II) produced in the first stage, with an acid to produce a 2-phenylacetophenone derivative of the formula (I).

(4) The process of (1), (2) or (3) wherein the compound of the formula (II) is reacted with a mineral acid.

(5) The process of (2) or (3) wherein the reaction of the first stage and the reaction of the second stage is continuously carried out in the same reactor.

(6) A process for producing a compound of the formula (IV), which comprises reacting a compound of the formula (V) with a compound of the formula (VI) and a compound of the formula (VII).

(7) A process for producing a compound of the formula (II), which comprises reacting a compound of the formula (III) with a compound of the formula (IV) in the presence of a base and a solvent.

(8) The process of (2), (3), (5) or (7), wherein the reaction to produce the compound of the formula (II) from the compound of the formula (III), is carried out in the presence of an inert gas.

(9) The process of (2), (3), (5), (7) or (8), wherein the reaction to produce the compound of the formula (II) from the compound of the formula (III), is carried out at a reaction temperature of from 0 to 100° C.

(10) The process of (9), wherein the reaction to produce the compound of the formula (II) from the compound of the formula (III), is carried out at a reaction temperature of from 0 to 40° C.

EXAMPLE 1

Preparation of 2-(4-fluorophenyl)-2-(N,N-dimethylamino)acetonitrile

Into a 1 l four-necked flask equipped with a thermometer, a stirrer and a dropping funnel, 49.6 g (0.4 mol) of 4-fluorobenzaldehyde and 480 ml of acetonitrile were charged, and a solution comprising 29.4 g (0.64 mol) of sodium cyanide, 81.6 g (1 mol) of dimethylamine hydrochloride and 200 ml of water, was dropwise added over a period of 15 minutes at from 20 to 30° C. with stirring, and then reacted at the same temperature for 18 hours. After completion of the reaction, the mixture was subjected to liquid separation. The organic layer was separated, and acetonitrile was distilled off. The residue was extracted with 400 ml of ethyl acetate, washed with a 5% sodium hydrogen carbonate aqueous solution and water, and then dried over anhydrous sodium sulfate. Ethyl acetate was distilled off, and the obtained oily substance was distilled under reduced pressure to obtain 64.5 g (yield: 90.5%) of the desired compound (boiling point: 100–101° C./1 KPa). The NMR spectrum data thereof are as follows.

$^1$H-NMR δ ppm (Solvent: CDCl$_3$/400 MHz) 2.29 (s, 6H), 4.79 (s, 1H), 7.07 (m, 2H), 7.48 (m, 2H)

EXAMPLE 2

Preparation of 2-(4-fluorophenyl)-2-(N,N-dimethylamino)acetonitrile

Into a 1 l four-necked flask equipped with a thermometer, a stirrer and a dropping funnel, 30.9 g (0.6 mol) of sodium cyanide, 85.7 g (1.05 mol) of dimethylamine hydrochloride, 1.2 g of benzyltri-n-butylammonium chloride and 200 ml of water were charged, and a solution comprising 62.1 g (0.5 mol) of 4-fluorobenzaldehyde and 150 ml of toluene, was dropwise added over a period of 30 minutes at from 20 to 30° C. with stirring, and then reacted at from 45 to 50° C. for 4 hours. After completion of the reaction, 200 ml of water was added, and the mixture was subjected to liquid separation. The organic layer was separated, washed with a 5% sodium hydrogen carbonate aqueous solution and water, and then dried over anhydrous sodium sulfate. Toluene was distilled off, and the obtained oily substance was distilled under reduced pressure to obtain 79.3 g (yield: 89%) of the desired compound (boiling point: 100–101° C./1 KPa).

EXAMPLE 3

Preparation of 1-(4-fluorophenyl)-2-(4-trifluoromethylphenyl)-N,N-dimethylethenylamine Into a 200 ml four-necked flask equipped with a thermometer, a stirrer, a dropping funnel and a N$_2$ gas supply tube, a N$_2$ gas was introduced so that the interior of the flask became a N$_2$ atmosphere. 40 ml of dimethylformamide and 2.4 g (61.6 mmol) of sodium hydride (62% oil suspension) were charged, and a solution comprising 10 g (56 mmol) of 2-(4-fluorophenyl)-2-(N,N-dimethylamino)acetonitrile and 10.9 g (56 mmol) of 4-(trifluoromethyl)benzyl chloride, was dropwise added over a period of one hour at from 5 to 10° C. under cooling with ice water and then further reacted at from 20 to 30° C. for one hour. After completion of the reaction, 200 ml of water was added, and the mixture was extracted with 200 ml of ethyl acetate. The extract was washed with a 5% sodium hydrogen carbonate aqueous solution and water and then dried over anhydrous sodium sulfate. Ethyl acetate was distilled off, and the obtained oily substance was distilled under reduced pressure to obtain 15.3 g (yield: 88.3%) of the desired compound (boiling point: 130–135° C./0.6 KPa). The NMR spectrum data thereof were as follows.

$^1$H-NMR δ ppm (Solvent: CDCl$_3$/400 MHz) 2.68 (s, 6H), 5.42 (s, 1H), 6.71 (m, 2H), 7.03 (m, 2H), 7.20 (m, 4H)

EXAMPLE 4

Preparation of 4'-fluoro-2-(4-trifluoromethylphenyl)acetophenone

Into a 200 ml four-necked flask equipped with a thermometer and a reflux condenser, 15.5 g (50 mmol) of 1-(4-fluorophenyl)-2-(4-trifluoromethylphenyl)-N,N-dimethylethenylamine, 80 ml of acetic acid and 30 ml of concentrated hydrochloric acid were charged and reacted with stirring for two hours under refluxing under heating by an oil bath. After completion of reaction, 500 ml of water was added, and precipitated crystals were collected by filtration and washed with a 2% sodium hydrogen carbonate aqueous solution and water. Then, the crystals were further washed and purified with 20 ml of n-hexane and then vacuum-dried to obtain 12.7 g (yield: 90.3%) of the desired compound (melting point: 93–95° C.) as slightly yellow crystals.

EXAMPLE 5

Preparation of 4'-fluoro-2-(4-trifluoromethylphenyl) acetophenone

Into a 1 l four-necked flask equipped with a thermometer, a stirrer, a dropping funnel and a $N_2$ gas supply tube, a $N_2$ gas was introduced so that the interior of the flask became a $N_2$ atmosphere. 250 ml of dimethylformamide and 16.5 g (0.426 mol) of sodium hydride (62% oil suspension) were charged, and a solution comprising 69 g (0.387 mol) of 2-(4-fluorophenyl)-2-(N,N-dimethylamino)acetonitrile and 75.4 g (0.387 mol) of 4-(trifluoromethyl)benzyl chloride, was dropwise added over a period of one hour at from 10 to 15° C. under cooling with ice water and then further reacted at from 20 to 30° C. for one hour. Then, 280 ml of 40% sulfuric acid was added to this reaction mixture and reacted at from 80 to 90° C. for one hour. After completion of the reaction, 2 l of water was added, and precipitated crystals were collected by filtration and washed with a 2% sodium hydrogen carbonate aqueous solution and water. Then, the crystals were further washed and purified with 100 ml of n-hexane and then vacuum-dried to obtain 97.7 g (yield: 89.4%) of the desired compound (melting point: 93–95° C.) as slightly yellow crystals.

EXAMPLE 6

Preparation of 2-(4-fluorophenyl)-2-(N,N-dimethylamino)acetonitrile

Into a 1 l four-necked flask equipped with a thermometer, a stirrer and a dropping funnel, 144.5 g (1.6 mol) of a 50.7% dimethylamine aqueous solution and 118.5 g of water were charged, and 159.4 g (0.38 mol) of a 25% of sulfuric acid aqueous solution was dropwise added over a period of 15 minutes at a temperature of not higher than 20° C. with stirring. Then, 67.4 g (1.38 mol) of sodium cyanide was introduced. Then, 155.1 g (1.25 mol) of 4-fluorobenzaldehyde was dropwise added over a period of 20 minutes at from 20 to 30° C. Thereafter, the reaction was carried out at 50° C. for 4 hours. After completion of the reaction, the reaction mixture was subjected to liquid separation. The organic layer was separated and washed with 500 ml of water of 50° C. to obtain 222.8 g (yield: 98.4%) of the desired compound having a purity of 98.4% (by GC analysis).

EXAMPLE 7

Preparation of 4'-fluoro-2-(4-trifluoromethylphenyl) acetophenone

Into a 2 l four-necked flask equipped with a thermometer, a stirrer, a dropping funnel and a $N_2$ gas supply tube, a $N_2$ gas was supplied so that the interior of the flask became a $N_2$ atmosphere. 400 ml of dimethylformamide and 35.0 g (0.9 mol) of sodium hydride (62% oil suspension) were charged, and a mixed solution comprising 133.5 g (0.75 mol) of 2-(4-fluorophenyl)-2-(N,N-dimethylamino)acetonitrile, 145.9 g (0.75 mol) of 4-(trifluoromethyl)benzyl chloride and 280 ml of dimethylformamide, was dropwise added over a period of one hour at from 10 to 25° C. under cooling with water and then further reacted at from 20 to 30° C. for one hour. Then, 330 g of 40% sulfuric acid aqueous solution was added to this reaction mixture and reacted at from 80 to 90° C. for one hour. After completion of the reaction, the reaction product was added to 2 e of water, and precipitated crystals were collected by filtration under reduced pressure and washed with water. Then, the crystals were washed and purified at 20° C. by means of 500 ml of isopropyl alcohol and then dried with hot air to obtain 204.7 g (yield: 95.2%) of the desired compound having a purity of 98.4% (by HPLC analysis).

INDUSTRIAL APPLICABILITY

According to the present invention, 2-phenylacetophenone derivatives which used to be difficult to produce on an industrial scale by conventional method, can be efficiently produced by a short reaction process by using a starting material which is industrially readily and inexpensively available.

What is claimed is:

1. A process for producing a 2-phenylacetophenone compound represented by the formula (I):

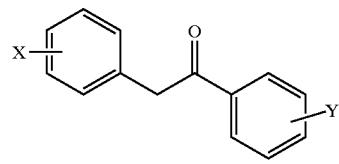

wherein X is an alkyl group or a haloalkyl group, and Y is a hydrogen atom, a halogen atom or an alkyl group which may be substituted, comprising reacting a compound represented by the formula (II):

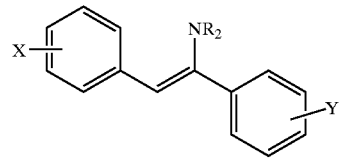

wherein X and Y are as defined above, and R is a hydrogen atom or an alkyl group with an acid.

2. The process for producing 2-phenylacetophenone compound according to claim 1, comprising:

(1) a first stage of reacting a compound represented by the formula (III):

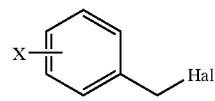

wherein X is a haloalkyl group, and Hal is a halogen atom with a compound represented by the formula (IV):

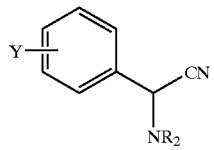

wherein Y is a hydrogen atom, a halogen atom or an alkyl group which may be substituted; and R is a hydrogen atom or an alkyl group in the presence of a base and a solvent, to produce a compound represented by the formula (II):

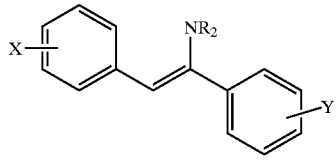

wherein X, Y and R are as defined above; and (2) a second stage of reacting the compound of the formula (II) produced in the first stage with an acid to produce a 2-phenylacetophenone derivative represented by the formula (I):

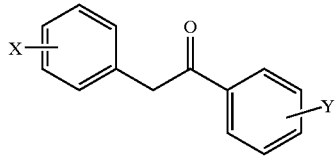

wherein X and Y are as defined above.

3. The process for producing 2-phenylacetophenone compound according to claim 2, comprising reacting a compound represented by the formula (V):

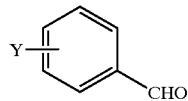

wherein Y is a hydrogen atom, a halogen atom or an alkyl group which may be substituted with a compound represented by the formula (VI): M-CN wherein M is an alkali metal element and a compound represented by the formula (VII): $R_2NH$ wherein R is a hydrogen atom or an alkyl group or its salt, to produce a compound represented by the formula (IV):

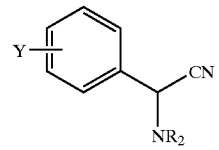

wherein Y and R are as defined above, which is subjected to the reaction of the first stage.

4. The process according to claim 1 or 2, wherein the acid is in a proportion of from 1 to 30 mols per mol of the compound of the formula (II).

5. The process according to claim 1 or 2, wherein the acid is a mineral acid.

6. The process according to claim 2, wherein the compound of the formula (IV) is in a proportion of from 0.9 to 5.0 mols per mol of the compound of the formula (III).

7. The process according to claim 2, wherein the base is in a proportion of from 1.0 to 2.0 mols per mol of the compound of the formula (III).

8. The process according to claim 2, wherein the first stage of reacting is in the presence of an inert gas.

9. The process according to claim 2, wherein the first stage of reacting is performed at a reaction temperature of from 0 to 100° C.

10. The process according to claim 2, wherein the first stage of reacting and the second stage of reacting are performed continuously in the same reactor.

11. A compound represented by the formula (II):

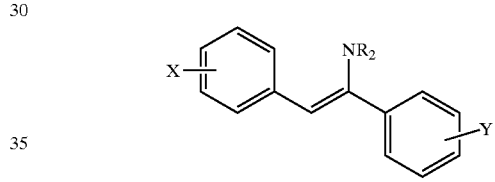

wherein X is a haloalkyl group, Y is a hydrogen atom, a halogen atom or an alkyl group which may be substituted, and R is a hydrogen atom or an alkyl group.

12. The compound of claim 11, wherein X is a difluoromethyl group.

13. The compound of claim 11, wherein Y is a hydrogen atom.

14. The compound of claim 11, wherein Y is a halogen atom.

15. The compound of claim 11, wherein Y is an alkyl group.

16. The compound of claim 11, wherein Y is a fluorine atom.

17. The process of claim 1, wherein Y is a hydrogen atom.
18. The process of claim 1, wherein Y is a halogen atom.
19. The process of claim 1, wherein Y is an alkyl group.
20. The process of claim 1, wherein Y is a fluorine atom.

* * * * *